United States Patent [19]

Kawai et al.

[11] Patent Number: 5,665,768

[45] Date of Patent: Sep. 9, 1997

[54] HETEROARYL CYCLOALKENYL HYDROXYUREAS

[75] Inventors: Akiyoshi Kawai; Rodney W. Stevens, both of Handa, Japan

[73] Assignee: Pfizer Inc., New York, N.Y.

[21] Appl. No.: 586,833

[22] PCT Filed: Jul. 5, 1994

[86] PCT No.: PCT/JP94/01093

§ 371 Date: Jan. 18, 1996

§ 102(e) Date: Jan. 18, 1996

[87] PCT Pub. No.: WO95/03292

PCT Pub. Date: Feb. 2, 1995

[30] Foreign Application Priority Data

Jul. 20, 1993 [JP] Japan ................... 5-179401

[51] Int. Cl.$^6$ ................... A61K 31/34
[52] U.S. Cl. ................... 514/471; 514/315; 514/449; 549/479
[58] Field of Search ................... 514/315, 445, 514/471; 549/479

[56] References Cited

U.S. PATENT DOCUMENTS

| 5,169,854 | 12/1992 | Brooks et al. | 514/314 |
| 5,187,192 | 2/1993 | Brooks et al. | 514/445 |
| 5,478,822 | 12/1995 | Hoshino et al. | 514/213 |
| 5,521,212 | 5/1996 | Ikeda et al. | 514/428 |

FOREIGN PATENT DOCUMENTS

| 89/04299 | 5/1989 | WIPO | 514/314 |
| 92/09566 | 6/1992 | WIPO | 514/314 |
| 92/09567 | 6/1992 | WIPO | 514/314 |

OTHER PUBLICATIONS

Kawai et al, Chemical Abstracts, vol. 120, #133, 919Q Mar. 1994.

*Primary Examiner*—James H. Reamer
*Attorney, Agent, or Firm*—Peter C. Richardson; Paul H. Ginsburg; Bryan C. Zielinski

[57] ABSTRACT

Certain novel heteroaryl cycloalkenyl hydroxyurea compounds having the ability to inhibit the 5-lipoxygenase enzyme and having formula (I) and the pharmaceutically acceptable salts thereof, wherein each $R^1$, independently, is hydrogen, hydroxy, chloro, fluoro, $C_1$–$C_4$ alkyl, $C_1$–$C_4$ alkoxy, $C_1$–$C_4$ haloalkyl or $C_1$–$C_4$ haloalkoxy; $R^2$ is hydrogen or $C_1$–$C_4$ alkyl; $R^3$ is hydrogen, chloro, fluoro or $C_1$–$C_4$ alkyl; X is O, S, SO or $SO_2$; Z is methylene or ethylene; A is divalent radical derived from furan, thiophene, pyridine, benzofuran, benzothiophene or quinoline, or one of these groups having one substituent selected from chloro, fluoro, $C_1$–$C_4$ alkyl, $C_1$–$C_4$ alkoxy, $C_1$–$C_4$ haloalkyl and $C_1$–$C_4$ haloalkoxy; n is 1, 2 or 3; and M is hydrogen or a pharmaceutically acceptable cation. These compounds are useful in the treatment or alleviation of inflammatory diseases, allergy and cardiovascular diseases in mammals and as the active ingredient in pharmaceutical compositions for treating such conditions.

10 Claims, No Drawings

HETEROARYL CYCLOALKENYL HYDROXYUREAS

TECHNICAL FIELD

This invention relates to novel N-hydroxyurea compounds. The compounds of the present invention inhibit the action of lipoxygenase enzyme and are useful in the treatment or alleviation of inflammatory diseases, allergy and cardiovascular diseases in mammals. This invention also relates to pharmaceutical compositions comprising such compounds.

BACKGROUND ART

Arachidonic acid is known to be the biological precursor of several groups of endogenous metabolites, prostaglandins including prostacyclins, thromboxanes and leukotrienes. The first step of the arachidonic acid metabolism is the release of arachidonic acid and related unsaturated fatty acids from membrane phospholipids, via the action of phospholipase A2. Free fatty acids are then metabolized either by cyclooxygenase to produce the prostaglandins and thromboxanes or by lipoxygenase to generate hydroperoxy fatty acids which may be further metabolized to the leukotrienes. Leukotrienes have been implicated in the pathophysiology of inflammatory diseases, including rheumatoid arthritis, gout, asthma, ischemia reperfusion injury, psoriasis and inflammatory bowel diseases. Any drug that inhibits lipoxygenase is expected to provide significant new therapy for both acute and chronic inflammatory conditions.

Recently several review articles on lipoxygenase inhibitors have been reported. (See H. Masamune and L. S. Melvin, Sr., Annual Reports in Medicinal Chemistry: 24 (1989) pp71–80 (Academic) and B. J. Fitzsimmons and J. Rokach, Leukotrienes and Lipoxygenases (1989) pp427–502 (Elsevier)).

More particularly, International Patent Publications Nos. WO 92/09566 and WO 92/09567, and U.S. Pat. No. 5,187,192, disclose a wide variety of N-hydroxyurea and hydroxamic acid compounds as inhibitors of the lipoxygenase enzyme. WO 92/09566 discloses some N-cycloalkenyl-N-hydroxyurea compounds having a heteroaryl substituent on the cycloalkene ring. However, none of the N-(heteroarylcycloalkenyl)-N-hydroxyurea compounds of WO 92/09566 has a further substituent containing an aromatic group attached to the heteroaryl group. In WO 92/09567 and U.S. Pat. No. 5,187,192, none of the N-hydroxyureas has an unsaturated ring (cycloalkene ring) attached to the N-hydroxyurea grouping.

BRIEF DISCLOSURE OF THE INVENTION

The present invention provides novel N-hydroxyurea compounds of the following chemical formula I:

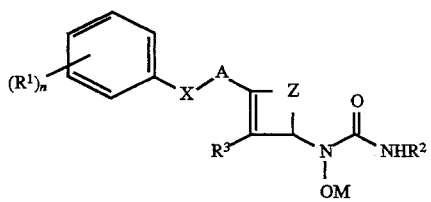

and the pharmaceutically acceptable salts thereof, wherein each $R^1$, independently, is hydrogen, hydroxy, chloro, fluoro, $C_1$–$C_4$ alkyl, $C_1$–$C_4$ alkoxy, $C_1$–$C_4$ haloalkyl or $C_1$–$C_4$ haloalkoxy; $R^2$ is hydrogen or $C_1$–$C_4$ alkyl; $R^3$ is hydrogen, chloro, fluoro or $C_1$–$C_4$ alkyl; X is O, S, SO or $SO_2$; Z is methylene or ethylene; A is divalent radical derived from furan, thiophene, pyridine, benzofuran, benzothiophene or quinoline, or one of these groups having one substituent selected from chloro, fluoro, $C_1$–$C_4$ alkyl, $C_1$–$C_4$ alkoxy, $C_1$–$C_4$ haloalkyl and $C_1$–$C_4$ haloalkoxy; n is 1, 2 or 3; and M is hydrogen or a pharmaceutically acceptable cation.

The compounds of the formula I inhibit the 5-lipoxygenase enzyme. Therefore the compounds are useful for treating a medical condition for which a 5-lipoxygenase inhibitor is needed, in a mammalian subject, e.g., a human subject. The compounds are especially useful for treating allergic and inflammatory conditions. This invention also embraces pharmaceutical compositions which comprise a compound of the formula I and a pharmaceutically acceptable carrier.

A preferred group of compounds of the invention consists of the compounds of the formula I, wherein $R^2$ and $R^3$ are each hydrogen, X is O or S, A is unsubstituted furan or unsubstituted thiophene and n is 1. Within this preferred group, particularly preferred compounds are those wherein $R^1$ is 4-fluoro; A is unsubstituted furan; and Z is ethylene.

Particularly preferred individual compounds of the invention are:

N-[3-[5-(4-Fluorophenoxy)-2-furyl]-2-cyclobuten-1-yl]-N-hydroxyurea;

N-[3-[5-(4-Fluorophenylthio)-2-furyl]-2-cyclopenten-1-yl]-N-hydroxyurea;

N-[3-[5-(4-Fluorophenoxy)-2-furyl]-2-cyclopenten-1-yl]-N-hydroxyurea;

[+]-N-[3-[5-(4-Fluorophenoxy)-2-furyl]-2-cyclopenten-1-yl]-N-hydroxyurea; and

[−]-N-[3-[5-(4-Fluorophenoxy)-2-furyl]-2-cyclopenten-1-yl]-N-hydroxyurea.

DETAILED DESCRIPTION OF THE INVENTION

In this application, the term "halo" is used to mean radicals derived from the elements fluorine and chlorine.

The term "pharmaceutically acceptable cation" refers to non-toxic cations including, but not limited to, cations based on the alkali and alkaline earth metals, such as sodium, lithium, potassium, magnesium, and the like, as well as non-toxic ammonium, substituted ammonium and quaternary ammonium cations, including, but not limited to, ammonium, tetramethylammonium, tetraethylammonium, methylammonium, diethylammonium, trimethylammonium, triethylammonium and the like.

The term "halo-substituted alkyl" refers to an alkyl radical as described above substituted with one or more halogens including, but not limited to, chloromethyl, bromoethyl, trifluoromethyl and the like. The preferred halo-substituted alkyl group is trifluoromethyl.

The term "halo-substituted alkoxy" is used to mean an alkoxy radical as described above substituted with one or more halogens including, but not limited to, chloromethoxy, bromoethoxy, difluoromethoxy, trifluoromethoxy and the like. The preferred halo-substituted alkoxy group is trifluoromethoxy.

General Synthesis

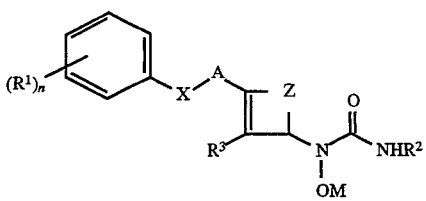

The compounds of formula I may be prepared by a number of synthetic methods. In the following formulae Q is,

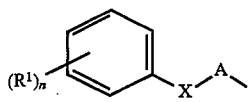

and $(R^1)_n$, X and A are as previously defined and M is hydrogen.

In one embodiment, compounds of the formula I are prepared according to the reaction steps outlined in Scheme 1:

Scheme 1

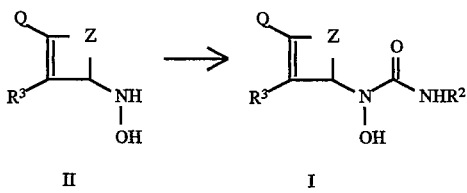

In this step the hydroxylamine II is treated with a suitable trialkylsilyl isocyanate or lower alkyl isocyanate in a reaction-inert solvent usually at ambient through to reflux temperature. Suitable solvents which do not react with reactants and/or products are, for example, tetrahydrofuran, dioxane, methylene chloride or benzene. An alternative procedure employs treatment of II with gaseous hydrogen chloride in reaction-inert solvent such as benzene or toluene and then subsequent treatment with phosgene. Reaction temperatures are usually in the range of ambient temperature through to boiling point of solvent. The intermediate carbamoyl chloride is not isolated but subjected to (i.e. in situ) reaction with aqueous ammonia or amine $H_2NR^2$. As a modification of this procedure, when $R^2$ is hydrogen, the acid addition salt of II may be reacted with an equimolar amount of alkali metal cyanate, such as potassium cyanate, in water. The product of formula I thus obtained is isolated by standard methods and purification can be achieved by conventional means, such as recrystallization and chromatography.

The aforementioned hydroxylamine II may be prepared by standard synthetic procedures from the corresponding cycloalkenone or cycloalkenol. For example, suitable cycloalkenone is converted to its oxime and then reduced to the requisite hydroxylamine II with a suitable reducing agent (for example, see R. F. Borch et al, *J. Am. Chem. Soc.*, 93, 2897 (1971). Reducing agents of choice are, but not limited to, sodium cyanoborohydride and boron-complexes such as borane-pyridine, borane-triethylamine and borane-dimethylsulfide, however, triethylsilane in trifluoroacetic acid may also be employed.

The suitable cyclobutenones or cyclopentenones can be prepared by a number of different approaches (see WO 92/09566). The cyclo-butenones may be prepared by the [2+2] cycloaddition of the corresponding ethylenes and dichloroketene followed by reductive dechlorination (for example, see R. L. Danheiser et al., *Tetrahedron Lett.*, 28, 3299 (1987). The cyclopentenones may be prepared by the intramolecular aldol cyclization of 1,4-diketones, readily accessible from the corresponding aldehydes and methyl vinyl ketone by the Stetter reaction (for example, see L. Novak et at., *Liebigs Ann. Chem.*, 509 (1986). Alternatively, the cycloalkenones can be prepared by the cross coupling reaction of, for example, the corresponding heteroaromatic halides or triflates with the cycloalkenylstannanes or vice versa in the presence of suitable catalyst such as $Pd(PPh_3)_4$, $PdCl_2(PPh_3)_2$ or the like (for example, see J. S. Kiely et al, *J. Heterocyclic Chem.*, 28, 1581 (1991)).

Alternatively, the aforementioned hydroxylamine II can easily be prepared by treating the corresponding cycloalkenol with N,O-bis(tert-butyloxycarbonyl)hydroxylamine under Mitsunobu-type reaction conditions followed by acid catalyzed hydrolysis (for example, employing trifluoroacetic acid) of the N,O-protected intermediate product IV ($R^4$ and $R^5$ are t-butyl) (see JP 1045344). The requisite cycloalkenol is readily prepared by the 1,2-reduction of the corresponding cycloalkenone using a suitable reducing agent such as sodium borohydride, sodium borohydride-cerium trichloride or the like.

The hydroxylamine of formula II thus obtained by the above-mentioned representative procedures is isolated by standard methods and purification can be achieved by conventional means, such as recrystallization and chromatography.

In another embodiment, compounds of the formula I are prepared as illustrated in Scheme 2. $R^4$ is phenyl, and $R^5$ is phenyl or lower alkyl:

Scheme 2

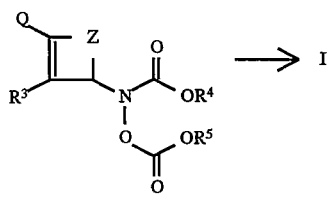

In this process, compound of formula III is prepared from the corresponding alcohol and a bis-carboxyhydroxylamine compounds, preferably N,O-bis(phenoxycarbonyl) hydroxylamine, and subsequently converted to I by treatment with ammonia, ammonium hydroxide, or an amine of structure $H_2NR^2$ (A. O. Stewart and D. W. Brooks., *J. Org. Chem.*, 57, 5020 (1992)). Suitable reaction solvents are, for example, methanol, ethanol, tetra. hydrofuran, benzene and the like, though reaction may be run in the absence of co-solvent, that is, in requisite amine alone. Reaction temperatures are typically in the range of ambient temperature through to boiling point of solvent. The product of formula I thus obtained is isolated by standard methods and purification can be achieved by conventional means, such as recrystallization and chromatography. The compounds of this invention can exist in stereoisomeric forms by virtue of the presence of one or more chiral centers. The present invention contemplates all such stereoisomers, including enantiomers, diastereomers, and mixtures. The individual isomers of compounds of the formula can be prepared by a number of methods known to those skilled in the art. For instance, by derivatization of a compound of formula I with a chiral auxiliary where the resulting diastereomeric mixture is separated and the auxiliary group cleaved to provide the desired isomer, or by separation employing a chiral stationary phase.

The pharmaceutically acceptable salts of the novel compounds of the present invention are readily prepared by contacting said compounds with a stoichiometric amount of, in the case of a non-toxic cation, an appropriate metal hydroxide or alkoxide or amine in either aqueous solution or a suitable organic solvent. In the case of non-toxic acid salt, an appropriate mineral or organic acid in either aqueous solution or a suitable organic solvent can be used. The salt may then be obtained by precipitation or by evaporation of the solvent.

Biological Activity

The compounds of the present invention inhibit the activity of lipoxygenase enzyme. This inhibition can be demonstrated in vitro by assays using Rat Peritoneal Cavity (RPC) resident cells, according to the method described in *Japanese Journal of Inflammation:* 7, 145–150 (1987) and using heparinized Human Whole Blood (HWB) cells, according to the method described in *Br. J. of Pharmacol.:* 99, 113–118 (1990), which determine the effect of said compounds on the metabolism of arachidonic acid. All of the products of the following examples were tested in the aforementioned assays and were shown to possess the efficacy of inhibiting lipoxygenase activity. In these tests, some preferred compounds show $IC_{50}$ values of 0.01 to 1 $\mu M$ in RPC assay and of 0.1 to 5 $\mu M$ in HWB assay, with respect to lipoxygenase activity.

The in vivo potency after oral administration of compounds of the invention to ICR mice (male) was determined using PAF lethality assay in a similar manner as described by J. M. Young et at. (J. M. Young, P. J. Maloney, S. N. Jubb, and J. S. Clark, *Prostaglandins*, 30, 545(1985). M. Criscuoli and A. Subissi, *Br. J. Pharmac.*, 90, 203(1987). H. Tsunoda, S. Abe, Y. Sakuma, S. Katayama, and K. Katayama, *Prostaglandins Leukotrienes and Essential Fatty Acids*, 39, 291 (1990)). In this test, some preferred compounds indicate $ED_{50}$ values in the range of 1 to 10 mg/kg p.o.

The ability of the compounds of the present invention to inhibit lipoxygenase enzyme makes them useful for controlling the symptoms induced by the endogenous metabolites arising from arachidonic acid in a mammalian subject. The compounds are therefore valuable in the prevention and treatment of such disease states in which the accumulation of arachidonic acid metabolites are the causative factor; e.g. allergic bronchial asthma, skin disorders, rheumatoid arthritis and osteoarthritis. Thus, the compounds of the present invention and their pharmaceutically acceptable salts are of particular use in the treatment or alleviation of inflammatory diseases in a human subject.

For treatment of the various conditions described above, the compounds of the formula I of this invention can be administered to a human subject either alone, or preferably in combination with pharmaceutically acceptable carriers or diluents in a pharmaceutical composition according to standard pharmaceutical practice.

The compounds can be administered to human subjects by various conventional routes of administration including oral and parenteral. When the compounds are administered orally to humans for the treatment or prevention of an inflammatory disease, the dose range will be from about 0.1 to 20 mg/kg of body weight of the subject to be treated per day, preferably from about 0.5 to 15 mg/kg of body weight per day, in single or divided doses. If parenteral administration is desired, then an effective dose will be from about 0.05 to 10 mg/kg of body weight of the human subject to be treated per day. In some instances it may be necessary to use dosages outside these limits, since the dosages will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules or as an aqueous solution or suspension. In the case of tablets for oral use, carriers which are commonly used include lactose and corn starch. Further lubricating agents such as magnesium stearate are commonly added. In the case of capsules, useful diluents are lactose and dried corn starch. When aqueous suspensions are required for oral use, the active ingredient is combined with emulsifing and suspending agents. If desired, certain sweetning and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solute should be controlled to make the preparation isotonic.

EXAMPLES

The present invention is illustrated by the following examples. However, it should be understood that the invention is not limited to the specific details of these examples. Proton nuclear magnetic resonance spectra (NMR) were measured at 270 MHz unless otherwise indicated and peak positions are expressed in parts per million (ppm) down field from tetramethylsilane. The peak shapes are denoted as follows: s—singlet, d—doublet, t—triplet, m—multiplet and br—broad.

Example 1

N-[3-[5-(4-Fluorophenoxy)-2-furyl]-2-cyclobuten-1-yl]-N-hydroxyurea

[A] 5-(4-Fluorophenoxy)-2-furfuraldehyde

To a stirred suspension of n-hexane washed NaH (60% W/V dispersion in mineral oil; 7.08 g; 177 mM) in THF (200 ml) under $N_2$ was added p-fluorophenol (19.9 g; 177 mM) in small portions in solid form. After gas evolution had ceased, solvent was removed in vacuo. The crude phenoxide was dissolved in DMF (200 ml) and cooled to 0° C., and to this stirred mixture was added 5-nitrofurfural (25 g; 177 mM) as a DMF solution (50 ml) via dropping funnel. During the addition, additional DMF (150 ml) was added. After addition was complete, the mixture was stirred 0.5 hour (hr) and poured into water. The whole was extracted with $Et_2O$ (300 ml×4, 200 ml×2), the combined organic layers washed with 10% NaOH (150 ml×3), water (150 ml×3), brine (150 ml×1), dried over $MgSO_4$, and passed through a short column of silica gel. The filtrate was evaporated in vacuo to provide 31 g of crude product, which was recrystallized from $Et_2O$-n-hexane to afford 26.9 g (yield 73.8%) of subtitle compound as a light yellow solid.

$^1$H-NMR (CDCl$_3$) δ; 9.41 (s, 1H), 7.22–7.05 (m, 5H), 5.53 (d, J=4.0 Hz, 1H) ppm.

[B] 2-[5-(4-fluorophenoxy)-2-furyl]-1,1-dibromoethene

Carbon tetrabromide (151 g; 455 mM), zinc dust (29.76 g; 455 mM) and triphenylphosphine (119.3 g; 455 mM) were combined in $CH_2Cl_2$ (1 L) and stirred overnight under $N_2$. To the resulting suspension was added a $CH_2Cl_2$ solution of aldehyde (37.5 g; 182 mM) and the mixture stirred for 3 hr at room temperature. Hexane (3 L) was added to the mixture and the hexane-$C_2Cl_2$ solution was filtered through a short column of silica gel topped with celite. The filtrate was concentrated to afford 59 g (yield 90%) of subtitle compound as a yellow oil.

[C] 2-[5-(4-Fluorophenoxy)-2-furyl]-ethyne

To a cooled (–78° C.), stirred solution of dibromo olefin (32 g; 88.4 mM) in THF (300 ml) was added dropwise n-butyllithium (113.4 ml; 176.9 mM, 1.56M in hexanes) under $N_2$. The reaction was stirred for 1 hr at –78° C. Aqueous saturated ammonium chloride (200 ml) was added to the cold reaction and the mixture was allowed to warm to room temperature. The solvent was removed, and water (200 ml) was added. The whole was extracted with $Et_2O$ (200 ml×2), and the combined organic layer washed with water (100 ml), brine (150 ml), dried over $MgSO_4$, and concentrated in vacuo. Chromatographic purification of the residue eluting with n-hexane provided 12.2 g (yield 68.5%) of subtitle compound.

[D] 3-[5-(4-Fluorophenoxy)-2-furyl]-4,4-dichloro-2-cyclobutenone

To a stirred suspension of acetylene (5.05 g; 25 mM) and zinc-copper couple (6.54 g; 100 mM) in $Et_2O$ (50 ml) was added dropwise trichloroacetyl chloride (8.37 ml; 75 mM) and phosphorus oxychloride (7 ml; 75 mM) at room temperature. After completion of addition, the mixture was refluxed overnight. After cooling, zinc-copper couple was filtered off. The filtrate was concentrated in vacuo, and $Et_2O$ (400 ml) was added. The whole was washed with water (200 ml×3), saturated aqueous $NaHCO_3$ (150 ml), water (150 ml), brine (200 ml), dried over $MgSO_4$, and filtered through a short column of silica gel to afford 6.4 g (yield 82%) of crude subtitle compound as a yellow oil, which was used without further purification.

1H-NMR ($CDCl_3$) δ; 7.37 (d, J=3.7 Hz, 1H), 7.23–7.10 (m, 4H), 6.14 (s, 1H), 5.63 (d, J=3.7 Hz, 1H) ppm.

[E] 3-[5-(4-Fluorophenoxy)-2-furyl]-2-cyclobutenone

To a stirred suspension of 3-[5-(4-fluorophenoxy)-2-furyl]-4,4-dichloro-2-cyclobutenone (6.4 g; 20 mM) in acetic acid (25 ml) was added zinc dust (6.5 g; 100 mM) at room temperature. After stirring for 2 hr, zinc was filtered off. The filtrate was evaporated in vacuo. The residue was purified by flash column ($SiO_2$) eluting with ethyl acetate-n-hexane (1:7) to give 2.2 g (yield 45%) of subtitle compound.

$^1$H-NMR ($CDCl_3$) δ; 7.19–7.06 (m, 4H), 6.80 (d, J=3.6 Hz, 1H), 5.99 (s, 1H), 5.55 (d, J=3.6 Hz, 1H), 3.45 (s, 2H) ppm.

[F] 3-[5-(4-Fluorophenoxy)-2-furyl]-2-cyclobutenone oxime

To a stirred solution of cyclobutenone (0.67 g; 2.75 mM) in EtOH-pyridine (10 ml-3 ml) was added hydroxylamine hydrochloride (0.29 g; 4.12 mM) at room temperature. The mixture was stirred overnight. The solvent was removed, and the resulting oil was taken up with ethyl acetate (100 ml). The whole was washed with 0.5N aqueous HCl (60 ml), and the aqueous layer extracted with ethyl acetate (50 ml), the combined organic layers washed with water (60 ml), brine (60 ml), dried over $MgSO_4$, and filtered through a short column of silica gel. The filtrate was concentrated in vacuo to provide 0.7 g of subtitle compound.

[G] N-[3-[5-(4-Fluorophenoxy)-2-furyl]-2-cyclobuten-1-yl]-N-hydroxyurea

To a stirred solution of 3-[5-(4-fluorophenoxy)-2-furyl]-2-cyclobutenoneoxime (0.87 g; 3.36 mM) in acetic acid (10 ml) was added $NaBH_3CN$ (0.3 g; 4.7 mM) at room temperature. After stirring for 1 hr, the reaction mixture was poured into 10% aqueous NaOH (80 ml). The whole was extracted with ethyl acetate (60 ml×2), and the combined organic layer washed with water (50 ml), brine (60 ml), dried over $MgSO_4$, and concentrated in vacuo to provide 0.9 g of crude hydroxylamine.

To a stirred solution of crude hydroxylamine (0.9 g; 3.45 mM) in THF (10 ml) was added trimethylsilyl isocyanate (TMSNCO) (0.61 g; 4.47 mM) at room temperature under $N_2$. The mixture was stirred for 30 min, and EtOH (10 ml) was added. Solvent was removed in vacuo, and the residue was recrystallized from ethyl acetate-n-hexane to provide 0.3 g (30%) of title compound as colorless solids.

m.p. 113°–116° C. (dec.);

$^1$H-NMR (DMSO-$d_6$) δ; 9.07 (s, 1H), 7.29–7.14 (m, 4H), 6.50 (d, J=3.6 Hz, 1H), 6.34 (s, 2H), 5.87 (s, 1H), 5.76 (d, J=3.6 Hz, 1H), 5.09 (br.s, 1H), 2.85–2.72 (m, 2H) ppm.

Anal. Calcd. for $C_{15}H_{13}FN_2O_4$: C, 59.21, H, 4.31, N, 9.21; found: C, 58.96, H, 4.20, N, 9.06.

Example 2

N-[3-[5-(4-Fluorophenylthio)-2-furyl]-2-cyclopenten-1-yl]-N-hydroxyurea

[A] 5-(4-Fluorophenylthio)-2-furfuraldehyde

To a stirred suspension of n-hexane washed NaH (60% dispersion in mineral oil; 3.6 g; 89 mM) in THF (100 ml) was added p-fluorothiophenol (11.4 g; 89 mM) in THF (10 ml) dropwise at ca 10° C. under $N_2$. After gas evolution ended, volatiles were removed in vacuo. The crude phenoxide was dissolved in DMF (75 ml) and cooled to 0° C., and to this mixture was added 5-nitrofurfural (12.5 g; 89 mM) in DMF (25 ml) via dropping funnel. The mixture was stirred for 0.5 hr, and then poured into water. The whole was extracted with $Et_2O$ (100 ml×5), the combined organic layer washed with aqueous 10% NaOH solution (100 ml×2), water (200 ml×2), brine (200 ml), dried over $MgSO_4$, and filtered through a short column of silica gel. The filtrate was concentrated in vacuo to provide 15 g (yield 87%) of the subtitle compound as a yellow oil.

1H-NMR ($CDCl_3$) δ; 9.56 (s, 1H), 7.50–7.42 (m, 2H), 7.27–7.18 (m, 1H), 7.10–6.96 (m, 2H), 6.53 (d, J=3.0 Hz, 1H) ppm.

[B] 1-[5-(4-Fluorophenylthio)-2-furyl]-1,4-pentanedione

To a stirred solution of 5-(4-fluorophenylthio)-2-furfuraldehyde (13.5 g; 60.8 mM) in EtOH (30 ml) was added methyl vinyl ketone (4.05 ml; 48.7 mM), 3-benzyl-5-(2-hydroxyethyl)-4-methylthiazolium chloride (2.84 g; 10.5 mM), and triethylamine (13.9 ml; 99.7 mM) at room temperature. After stirring overnight, volatiles were removed. To the residue was added water (150 ml), and the whole was extracted with ethyl acetate (100 ml×2). The combined organic layer washed with water (70 ml), brine (70 ml), dried over MgSO$_4$, and concentrated in vacuo. The residual oil was purified by flash column chromatography (SIO$_2$) eluting with ethyl acetate-n-hexane (1:4) to give 15.7 g (yield 89%) of the subtitle compound as a yellow oil.

$^1$H-NMR (CDCl$_3$) δ; 7.44–7.36 (m, 2H), 7.17 (d, J=3.6 Hz, 1H), 7.04 (t, J=8.8 Hz, 2H), 6.57 (d, J=3.6 Hz, 1H), 3.09 (t, J=6.2 Hz, 2H), 2.84 (t, J=6.2 Hz, 2H), 2.22 (s, 3H) ppm.

[C] 3-[5-(4-Fluorophenylthio)-2-furyl]-2-cyclopentenone

A solution of 1-[5-(4-fluorophenylthio)-2-furyl]-i ,4-pentanedione (8 g; 27.4 mM) in 0.55M aqueous NaOH solution (100 ml) was refluxed for 5 hr. After cooling, the whole was extracted with Et$_2$O (150 ml×1, 90 ml×2). The combined extract was washed with water (90 ml), brine (150 ml), dried over MgSO$_4$, and filtered through a short column of silica gel. The filtrate was concentrated in vacuo to give 5.9 g (yield 79%) of the subtitle compound as a black oil.

$^1$H-NMR (CDCl$_3$) δ; 7.39–7.30 (m, 2H), 7.06–6.99 (m, 2H), 6.82 (d, J=3.7 Hz, 1H), 6.68 (d, J=3.3 HZ, 1H), 6.38 (t, J=1.8 Hz, 1H), 2.90 (d.t, J=1.8 Hz, 5.2 Hz, 2H), 2.52 (t, J=5.2 Hz, 2H) ppm.

[D] 3-[5-(4-Fluorophenylthio)-2-furyl]-2-cyclopentenone oxime

To a stirred solution of 3-[5-(4-fluorophenylthio)-2-furyl] -2-cyclopentenone (5.9 g; 21.5 mM) in EtOH-pyridine (50 ml-12 ml) was added hydroxylamine hydrochloride (2.24 g; 32.3 mM) at room temperature. After stirring overnight, solvent was removed. To the residue was added 0.5N aqueous HCl (80 ml), and the whole was extracted with ethyl acetate (100 ml×2). The combined organic layer was washed with water (70 ml), brine (70 ml), dried over MgSO$_4$, and concentrated in vacuo to give 6 g (yield 97%) of crude subtitle compound as a brown oil, which was used without further purification.

[E] N-[3-[5-(4-Fluorophenylthio)-2-furyl]-2-cyclopenten-1-yl]-N-hydroxylamine

To a stirred solution of 3-[5-(4-fluorophenylthio)-2-furyl] -2-cyclopentenone oxime (6 g; 20.8 mM) in acetic acid (40 ml) was added NaBH$_3$CN (1.57 g; 24.9 mM) at room temperature. After stirring for 2.5 hr, acetic acid was removed. The residue was dissolved in ethyl acetate (150 ml), and the whole was washed with saturated aqueous NaHCO$_3$ (80 ml). The aqueous layer was extracted with ethyl acetate (80 ml), and the combined organic layer washed with water (80 ml), brine (80 ml), dried over MgSO$_4$, and concentrated in vacuo. Chromatographic purification of the residue during with CH$_2$Cl$_2$-EtOH (50: 1) provided 1.35 g (yield 22%) of the subtitle compound as a yellow oil.

$^1$H-NMR (CDCl$_3$) δ; 7.28–7.22 (m, 2H), 6.98 (t, J=8.8 Hz, 2H), 6.68 (d, J=3.3 Hz, 1H), 6.34 (d, J=3.3 Hz, 1H), 6.11 (br.s, 1H), 4.32 (br.s, 1H), 2.83–2.73 (m, 1H), 2.66–2.55 (m, 1H), 2.33–2.22 (m, 1H), 2.05–1.94 (m, 1H) ppm.

[F] N-[3-[5-(4-Fluorophenylthio)-2-furyl]-2-cyclopenten-1-yl]-N-hydroxyurea

To a stirred solution of N-[3-[5-(4-fluorophenylthio)-2-furyl]-2-cyclopenten-1-yl]-N-hydroxylamine (1.35 g; 4.64 mM) in THF (13 ml) was added TMSNCO (0.755 g; 5.56 mM) at room temperature under N$_2$. After stirring for 1 hr, EtOH (20 ml) was added. Volatiles were removed, and the resulting residue was recrystallized from ethyl acetate-EtOH (20 ml–120 ml) to provide 0.5 g of the title compound as a colorless solid.

m.p. 184°–186° C. (dec.);

1H-NMR (DMSO-d$_6$) δ; 8.95 (s, 1H), 7.31–7.18 (m, 4H), 6.99 (d, J=3.3 Hz, 1H), 6.59 (d, J=3.3 Hz, 1H), 6.34 (s, 2H), 5.90 (br.s, 1H), 5.32 (br.s, 1H), 2.71–2.59 (m, 1H), 2.53–2.43 (m, 1H), 2.17–2.05 (m, 1H), 1.98–1.84 (m, 1H) ppm.

Anal. Calcd. for C$_{16}$H$_{15}$FN$_2$O$_3$S: C, 57.48, H, 4.52, N, 8.38, F, 5.68, S, 9.59; found: C, 57.52, H, 4.46, N, 8.30, F, 5.65, S, 9.78.

Example 3

N-[3-[5-(4-Fluorophenoxy)-2-furyl]-2-cyclopenten-1-yl]-N-hydroxyurea

The title compound was prepared according to the procedure of Example 2 using 5-(4-fluorophenoxy)-2-furfuraldehyde instead of 5-(4-fluorophenylthio)-2-furfuraldehyde in step [B].

m.p. 153°–156° C. (dec.);

$^1$H-NMR (DMSO-d$_6$) δ; 8.91 (s, 1H), 7.29–7.14 (m, 4H), 6.42 (d, J=3.3 Hz, 1H), 6.32 (s, 2H), 5.74 (d, J=3.3 Hz, 1H), 5.67 (d, J=1.9 Hz, 1H), 5.29 (br.s, 1H), 2.66–2.38 (m, 2H), 2.13–2.04 (m, 1H), 1.94–1.85 (m, 1H) ppm.

Anal. Calcd. for C$_{16}$H$_{15}$FN$_2$O$_4$: C, 60.38, H, 4.75, N, 8.80; found: C, 60.51, H, 4.70, N, 8.59.

Examples 4 and 5

[+]-N-[3-[5-(4-Fluorophenoxy)-2-furyl]-2-cyclopenten-1-yl]-Nhydroxyurea and

[−]-N-[3-[5-(4-Fluorophenoxy)-2-furyl]-2-cyclopenten-1-yl]-N-hydroxyurea

The title compounds were obtained by chiral separation of the racemate obtained in Example 3. The racemate (50 mg) was resolved by HPLC (eluant; n-hexane-EtOH (70:30)) using chiral column (DAICEL chiral pak AS) to give 20 mg of the less polar enantiomer as a colorless solid (Example 4);

m.p. 151.5°–153° C. (dec.); [α]$_D$=+42.5° (c=0.04, EtOH), and 19 mg of the more polar enantiomer as a colorless solid (Example 5);

m.p. 151.5°–153° C. (dec.); [α]$_D$=−40.0° (C=0.04, EtOH).

We claim:

1. A compound of the following chemical formula:

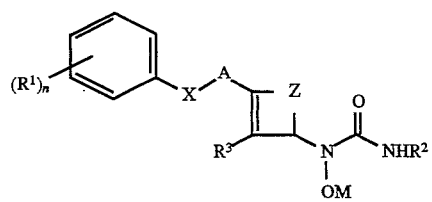

and the pharmaceutically acceptable salts thereof, wherein each R$^1$, independently, is hydrogen, hydroxy, chloro, fluoro, C$_1$–C$_4$ alkyl, C$_1$C$_4$ alkoxy, C$_1$–C$_4$ haloalkyl or C$_1$–C$_4$ haloalkoxy;

R$^2$ is hydrogen or C$_1$–C$_4$ alkyl;

$R^3$ is hydrogen, chloro, fluoro or $C_1$–$C_4$ alkyl;

X is O, S, SO or $SO_2$;

Z is methylene or ethylene;

A is divalent radical derived from furan, thiophene, pyridine, benzofuran, benzothiophene or quinoline, or one of these groups having one substituent selected from chloro, fluoro, $C_1$–$C_4$ alkyl, $C_1$–$C_4$ alkoxy, $C_1$–$C_4$ haloalkyl and $C_1$–$C_4$ haloalkoxy;

n is 1, 2 or 3; and

M is hydrogen or a pharmaceutically acceptable cation.

2. A compound according to claim 1 wherein X is O or S; and A is unsubstituted furan or unsubstituted thiophene.

3. A compound according to claim 2 wherein $R^2$ is hydrogen; $R^3$ is hydrogen; and n is 1.

4. A compound according to claim 3 wherein Z is ethylene.

5. A compound according to claim 4 wherein $R^1$ is 4-fluoro; and A is unsubstituted 2,5-divalent furan.

6. A compound according to claim 1 wherein the compound is selected from:

N-[3-[5-(4-Fluorophenoxy)-2-furyl]-2-cyclobuten-1-yl]-N-hydroxyurea;

N-[3-[5-(4-Fluorophenylthio)-2-furyl]-2-cyclopenten-1-yl]-N-hydroxyurea;

N-[3-[5-(4-Fluorophenoxy)-2-furyl]-2-cyclopenten-1-yl]-N-hydroxyurea;

[+]-N-[3-[5-(4-Fluorophenoxy)-2-furyl]-2-cyclopenten-1-yl]-N-hydroxyurea; and

[−]-N-[3-[5-(4-Fluorophenoxy)-2-furyl]-2-Cyclopenten-1-yl]-N-hydroxyurea.

7. A method for treating an allergic or inflammatory condition in a mammalian subject, which comprises administering to said subject a therapeutically effective amount of a compound according to claim 1.

8. A pharmaceutical composition for the treatment of an allergic or inflammatory condition in a mammalian subject which comprises a therapeutically effective amount of a compound of claim 1 and a pharmaceutically acceptable carrier.

9. A compound according to claim 1, wherein $R^1$ is 4-fluoro; $R^2$ and $R^3$ are each hydrogen; X is O or S; Z is methylene or ethylene; A is unsubstituted 2,5-divalent furan, and n is 1.

10. A compound according to claim 9, wherein X is O and Z is ethylene.

\* \* \* \* \*